United States Patent [19]

Sablotsky

[11] Patent Number: 4,994,267

[45] Date of Patent: Feb. 19, 1991

[54] TRANSDERMAL ACRYLIC MULTIPOLYMER DRUG DELIVERY SYSTEM

[75] Inventor: Steven Sablotsky, Miami, Fla.

[73] Assignee: Noven Pharmaceuticals, Inc., Miami, Fla.

[21] Appl. No.: 295,847

[22] Filed: Jan. 11, 1989

Related U.S. Application Data

[63] Continuation-in-part of Ser. No. 164,482, Mar. 4, 1988, Pat. No. 4,814,168.

[51] Int. Cl.$^5$ .............................................. A61K 31/74
[52] U.S. Cl. ..................................... 424/78; 424/484; 424/485; 424/486; 424/448; 424/449
[58] Field of Search ................ 424/484, 485, 486, 70, 424/448, 449

[56] References Cited

U.S. PATENT DOCUMENTS 4,568,343  2/1986  Leeper et al. ...................... 424/449
4,573,996  3/1986  Kwiatek et al. ................... 424/449
4,906,475  3/1990  Kim ................................... 424/449

Primary Examiner—Merrell C. Cashion, Jr.
Assistant Examiner—Leon R. Jones
Attorney, Agent, or Firm—Sybil Meloy

[57] ABSTRACT

A dermal composition comprising a drug, a multipolymer of ethylene-vinyl acetate, an acrylic polymer, and optionally one or more monomers, a natural or synthetic rubber and a tackifying agent. The ratio of the multipolymer to the rubber is, respectively, about 1:1 to about 10:1 and more preferably, 1:1 to 5:1 and more preferably 3:1. The dermal composition can optionally contain a crosslinking agent, tackifiers, penetration enhancers and other ingredients known for use in adhesives for the transdermal delivery of drugs. The dermal compositions can be produced by a variety of methods known in the preparation of drug containing adhesive preparations including the homogenous mixing of the multipolymer, drug and optional crosslinking agent and additional ingredients in solution or suspension or emulsion followed by removal of excess solvent.

14 Claims, No Drawings

TRANSDERMAL ACRYLIC MULTIPOLYMER DRUG DELIVERY SYSTEM

CROSS-REFERENCE TO RELATED APPLICATION

This application is a continuation in part of U.S. Pat. Application Ser. No. 164,482, filed March 4, 1988, now under U.S. Pat. No. 4,814,168, granted Mar. 21, 1989, now U.S. Pat. No. 0,814,168, which Application Serial No. 164,482 is incorporated herein by reference. Applications are assigned to Noven Pharmaceuticals, Inc. of Miami, Fla.

BACKGROUND OF THE INVENTION

The use of a pressure sensitive adhesive containing a medicament, i.e., a drug, as a means of drug delivery through the skin at essentially a constant rate, is well known.

Known delivery systems involve incorporation of a medicament into the pressure sensitive adhesive formulation. The pressure sensitive adhesive must adhere effectively to the skin and then permit migration of the medicament from the pressure sensitive adhesive through the skin and into the blood stream of the patient.

Transdermal pressure sensitive adhesive formulations, such as nitrate vasodilators, may involve high concentrations (10 to 40% by weight) of the medicament in the adhesive. This type and high concentration of medicament markedly reduces the desirable adhesion properties of the adhesive, particularly when the drug serves as a plasticizer, namely a solvent, for the adhesive. The result is a marked reduction in the cohesive strength of the adhesive. Thus, peel adhesion, tack and shear resistance suffer undesirably due to the medicament addition. The incorporation of crosslinking agents for reactive functional groups of the polymer may, for example, enhance the formulation's shear resistance, but at the expense of tack and peel adhesion.

The use of presently marketed nitrate vasodilators in a pressure sensitive adhesive has been reported to frequently result in partial or total debonding, as early as during the first 24 hours of wearing by the patient. This debonding occurs as the patient perspires, exercises, or undertakes the normal physical activities expected in such a situation. The undesirable debonding results in a reduced rate of medication delivery and a total dosage reduction proportional to the area of the device which is no longer in contact with the skin. A stronger adhesive, namely one having higher peel adhesion, shear resistance and tack, and in addition being perspiration resistant, would more effectively resist such undesirable debonding.

Transdermal pressure sensitive adhesive formulations may also involve low concentrations (5% or less by weight) of the medicament in the adhesive. When an adhesive formulation containing a low concentration of the drug is used, although the lower concentration of the medicament in the adhesive does not critically affect the peel adhesion, tack and shear resistance of the formulation in the presence of sufficient plasticizer, difficulties are experienced in the release rate of the medicament from the adhesive.

Previous adhesives have used as their starting polymer one that is inherently tacky. This invention utilizes an inherently tacky adhesive in combination with a non-tacky polymer.

SUMMARY OF THE INVENTION

This invention is directed to a dermal composition suitable for use in the transdermal delivery of drugs, which composition permits a high loading of medicament as well as a low loading of medicament into the formulation while maintaining acceptable shear, tack and peel adhesive properties.

The dermal composition of this invention comprises a drug; a multipolymer comprising an ethylene/vinyl acetate polymer and an acrylate polymer; a rubber; and a tackifying agent. The multipolymer and rubber are preferably in a ratio, respectively, from about 1:10 to about 30:1, preferably about 1:5 to 20:1 and more preferably about 1:2 to about 15:1. The ratio of ethylene/vinyl acetate polymer to acrylate polymer is preferably about 20:1 to about 1:20 by weight. The ethylene/vinyl acetate polymer can be a copolymer, or a terpolymer including for example an acrylic and/or methacrylic acid group. The multipolymer can include mixtures of polymers such as copolymers or terpolymers of ethylene/vinyl acetate or a mixture of the same with a different polymer and a polyacrylate or polymethacrylate. The composition can additionally contain or employ other ingredients known for use in pressure sensitive adhesives including crosslinking agents, plasticizers, fillers and anti-oxidants.

The multipolymer is prepared by combining the acrylate polymer or polymers with the ethylene/vinyl acetate polymer or polymers. The composition is prepared by mixing the drug and the multipolymer, with an elastomer, namely the rubber and a tackifying agent.

It has been found that when the transdermal formulations described in U.S. Ser. No. 164,482, filed Mar. 4, 1988 are used with drugs constituting less than 50% by weight of the dermal composition and especially with drugs constituting less than 10% and even more especially with drugs constituting less than 5% of the total weight of the dermal composition, adequate or improved release rate is achieved while maintaining necessary peel adhesion, shear resistance and tack by incorporation into the composition of an acrylic polymer. The composition maintains its adhesive properties even where the drug acts as a plasticizer or solvent. The tackifying agent increases tack and adhesiveness.

Although the structure of the composition has not been analyzed, it is conceivable that all the resins, namely the rubber, and the multipolymer comprising the ethylene/vinyl acetate polymer and the acrylate polymer, result in a heterogenous mix, the components of the polymeric mixture performing as a mutually interpenetrating polymeric network in the composition. In other words, the adhesive composition is a mixture of essentially non-mutually soluble or immisible in solution polymers. In contradistinction to the typical prior transdermal drug systems composed of a single polymer or mutually soluble polymers (in solution).

DETAILED DESCRIPTION OF THE INVENTION

This invention is directed to multipolymer dermal compositions suitable for transdermal drug delivery. The dermal compositions of this invention are resistant to erosion by moisture and biological fluids and yet have strong peel adhesion, shear resistance and tack qualities.

The dermal composition of this invention comprises a drug; a multipolymer comprising an ethylene/vinyl acetate polymer and an acrylate polymer; a rubber and a tackifying agent. The multipolymer and rubber are preferably in a ratio by weight respectively from about 1:10 to about 30:1, more desirably 1:5 to 20:1 and preferably about 1:2 to about 15:1. The ratio of ethylene/vinyl acetate polymer to acrylate polymer is preferably about 20:1 to about 1:20 by weight. A crosslinking agent for any reactive functional groups on the polymer may optionally be used as will be apparent to one skilled in the art. Crosslinking agents for this system are those known for use in crosslinking of carboxyl groups.

This system permits an unusually low loading of medicament into the dermal composition while maintaining the desirable physical properties and release rate.

The transdermal drug delivery system of this invention has a defined geometric shape, with a release liner on one side. Removal of the liner exposes the pressure sensitive adhesive that functions as the drug carrier and as the means of applying the system to the patient. The pressure-sensitive adhesive is backed by a drug impermeable material that may be colored and labeled as appropriate. Suitable release liners and backings include those known in the art for use with pressure sensitive adhesives.

The composition of this invention possesses sufficient adhesive properties to remain in place for days with low incidence of debonding and appears, surprisingly, to modify the cohesive strength, peel and tack of over that of a transdermal drug delivery system lacking a rubber or lacking an ethylene/vinyl acetate polymer or both.

It has been surprisingly found that the addition of a rubber and ethylene/vinyl acetate polymer to an acrylic pressure sensitive adhesive formulation results in a pressure sensitive drug adhesive dermal composition of desirable peel, adhesion, shear resistance and tack, especially adapted for use with the delivery of drugs where the weight of the drug is less than 50% of the total weight of the composition, and more preferably where the weight of the drug is less than 10% or more, preferably less than 5% of the total weight of the composition.

This invention is based on the finding that the adhesive properties of drug-containing dermal composition containing a rubber and ethylene/vinyl acetate polymer can be improved by the addition of an acrylate polymer and, where low percentages of drug are involved, by the addition of a major amount of an acrylate polymer.

The dermal composition according to the present invention can be prepared, for example, by mixing the multipolymer including the acrylate polymer, drug, the rubber and tackifying agent in an appropriate liquid, preferably an organic liquid, such as alcohols such as isopropyl alcohol, ethanol, benzenes such as xylene and toluene, alkanes and cycloalkanes such as hexane, heptane, cyclohexane, and alkanoic acid acetates such as an ethyl acetate, casting the mixture and removing the liquid; for example by evaporation, to form a film.

The ethylene/vinyl acetate copolymers can be either a copolymer or a terpolymer. Thus a copolymer of vinyl acetate and ethylene can be used. A terpolymer of an acrylic acid/ethylene/vinyl acetate can also be used. Thus the third monomer of the terpolymer can be an acrylic acid such as acrylic acid or methacrylic acid or copolymers thereof.

The poly-acrylic polymer of the multipolymer can be any of the various homopolymers, copolymers, terpolymers and the like of various acrylic acids. The acrylic polymer constitutes preferably from about 5% to about 95% to total weight of the multipolymer, and preferably 25% to 90%, the amount of the acrylate polymer being chosen being dependent on the amount and type of the drug used. Thus the smaller the amount of the drug used, the greater amount of the acrylate polymer can be used.

The acrylate polymers of this invention are polymers of one or more acrylic acids and other copolymerizable functional monomers. By varying the amount of monomer added, the cohesive properties of the resulting acrylate polymer can be changed, and the release rate or release amount of active ingredient may be controlled. It is also possible to increase the hydrophilic properties of the polymer by selecting appropriate types of monomers.

The acrylate polymers include copolymers of alkyl acrylates or methacrylate and/or copolymerizable functional monomer.

The acrylate polymer is composed of at least 50% by weight of an acrylate or alkyl-acrylate, from 0 to 20% of a functional monomer copolymerizable with the acrylate and from 0 to 40% of other monomers.

Polyacrylates which can be used include acrylic acid, methacrylic acid and N-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Funtional monomers copolymerizable with the above alkyl acrylates or methacrylates which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Ethylene/vinyl acetate copolymers and terpolymers are well known, commercially available materials. Typically such polymers have a vinyl acetate content of about 4 percent to 80 percent by weight and an ethylene content of 15 to 90 percent of the total. Melt index is the number of grams of polymer which can be forced through a standard cylindrical orifice under a standard pressure at a standard temperature and thus is inversely related to molecular weight. As is used in the specification, melt index is determined in accordance with the standard ASTM D 1238-65DP. Preferably the ethylene/vinyl acetate copolymer or terpolymer has a vinyl acetate content of about 4 percent to 50 percent by weight, with a melt index of about 0.5 to 250 grams per ten minutes, and a density having a range of about 0.920 to 0.980. More preferably the polymer has a vinyl acetate content of 4 percent to 40 percent by weight and a melt index of about 0.5 to 25 grams per ten minutes.

In addition to varying the percentage of vinyl acetate in the ethylene/vinyl acetate polymer, the properties of the polymer can be changed by varying the amount of acrylate polymer.

From the foregoing it can be understood that the multipolymer can be composed of an ethylene/vinyl acetate polymer containing at least about from 15 to 90 percent by weight of ethylene monomer and from about 4 to 80 percent by weight of vinyl acetate monomer, and from about 5 to 95% of an acrylate polymer.

The ethylene/vinyl acetate and acrylate multipolymer is permeable to the drug and thus permits passage of the drug by diffusion through the polymer. Normally, the rate of passage of the drug through the polymer is dependent on the solubility of the drug therein. This means that the selection of the particular ethylene/vinyl acetate and acrylate multipolymer, along with the rubber and other agents will be dependent on the particular drug used and the form in which it is added, namely drug alone or the drug plus solvent. By varying the composition, the dosage delivery rate can be controlled as will be apparent to one skilled in the art To the extent the tackifying agent is a natural or synthetic rubber, references herein to amounts of a rubber in the composition includes the rubber used as a tackifyer.

Selection of the particular multipolymer is governed in large part by the drug to be incorporated in the device, as well as the desired rate of delivery of the drug. Those skilled in the art can readily determine the rate of delivery of drugs from the polymers and select suitable combinations of polymer and drug for particular applications. Various techniques can be used to determine the rate of delivery of the drug from the polymer. The rate of delivery is easily determined by measuring the rate of drug transferred from one chamber to another through cadaver skin and calculating, from the obtained data, the drug delivery or flux rate.

The term "rubber" used here means a natural or synthetic elastomeric polymer. The rubbers useful in the invention include natural latex (polyisoprene) and carboxylated styrene/butadiene polymers. Other suitable rubbers include styrene copolymers such as styrene-isoprene-styrene block copolymer, polybutylene and polyisobutylene, synthetic polyisoprene, butyl rubber and silicone rubber.

The rubber elastomers impart the properties of rubber to the composition such as extensibility and rapid recovery from modular strains. Particularly suitable elastomers include the synthetic rubbers having a molecular weight distribution approximating that of natural rubber latex or natural rubber latex itself, such as styrene-butadiene rubber.

The ratio by weight of multipolymer to rubber is preferably about 1:10 to about 30:1 respectively and more preferably about 1:5 to about 20:1, and even more preferably 1:2 to 15:1, the amount of rubber used being selected to preferably achieve a tack of 200 to 800 grams per square centimeter and more preferably 300 to 500 grams per square centimeter (ASTM D 2979) and adhesion of about 1 to 3 pounds per linear inch (ASTM D 903-49).

In general, the composition should have a glass transition temperature (Tg), measured using a differential scanning calorimeter, of between about −70° C. to 0° C. and be a pressure sensitive adhesive at room temperature.

In practicing the invention, one may use any drug capable of producing a pharmacological response, either localized or systemic in animals and plants. The active drugs that can be administered by the novel transdermal drug delivery system of this invention include, but are not limited to:

1. Cardiovascular medications, such as, nitroglycerin, isosorbide dinitrate, isosorbide mononitrates, diltiazem, nifedipine, quinidine sulfate, procainamide, clonidine, propranolol, and others;

2. Hormones including steroids, such as, androgens, estrogens, and progestational agents;

3. Anesthetics, such as, lidocaine, fentanyl, fentanyl analogues, and the like;

4. Analgesics and drugs having an action on the central nervous system, such as, salicylic acid derivatives, opiates, opioids and antagonists therefor;

5. Nutritional agents, such as, vitamins and amino acids;

6. Anti-inflammatory agents, such as, piroxicam, indomethacin, prednisolone, and steroids;

7. Antihistamines and cold-remedy entities, such as, chlorpheniramine maleate, and phenylpropanolamine;

8. Respiratory agents, such as, salbutamol and terbutaline;

9. Sedatives and hypnotics, such as chloral hydrate, benzodiazepines, and barbiturates;

10. Anti-infectives, such as, antibiotics and antivirals;

11. Dermatological agents;

12. Anti-cancer drugs;

13. Anti-diabetics; and

14. Anorectics.

Other drugs having the same or different physiological activity as those cited above, may be used within the scope of this invention.

The amount of drug to be incorporated in the composition varies depending on the particular drug, the desired therapeutic effect and the time span for which the device provides therapy. For most drugs, the passage of the drugs through the skin will be the rate limiting step. Thus the amount of drug and the rate of release is typically selected so as to provide delivery characterized by a zero order time dependency for a prolonged period of time. The minimum amount of drug in the system is selected based on the rate at which the drug passes through the skin in the time span for which the device is to provide therapy. Conveniently the amount of drug in the system can vary from about 0.1 to about 50% by weight and preferably for the lower drug doses permitted by this invention is about 1 to 30%.

The drugs in the multipolymer, can be in different forms, depending on the form which yields the optimum release characteristics. Thus, the drugs can be in their free base or acid form, in the form of salts, esters or ethers, components of molecular complexes or pharmacologically acceptable derivatives thereof.

Tackifying agents for use in this invention are those known in the art including: (1) aliphatic hydrocarbons, for example, polyisobutylene; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. Tackifying agents can be classified into those containing polar groups and those without polar groups. Tackifying agents with polar groups include natural rosin, hydrogenated rosin and derivatives thereof such as the glycerin or pentaerytritol esters. Tackifying agents without polar groups include polyterpenes and the so-called petroleum based tackifiers produced by polymerization of petroleum cracking fractions, mainly C5 to C9 cracking fractions.

Crosslinking agents of this invention are those groups known in the art for crosslinking carboxylic acid groups including: (1) melamine formaldehyde resin; (2) urea formaldehyde resin; (3) phenolic resin; (4) glyoxal; (5) zinc oxide and magnesium oxide and (6) ammonium dichromate.

The optional inclusion of a crosslinking agent causes the formation of a three dimensional molecular lattice network, which serves to increase the structural integrity without solubilizing or otherwise interfering with the adhesive properties of the composition.

By adjusting the type and amount of multipolymer, rubber, drug, tackifying agent and optional crosslinking agent, it is possible to produce a composition that can be effectively utilized as a transdermal drug delivery system. The interacting effects of the drug, multi-polymer, rubber, tackifying agent and optional crosslinking agent make it possible to improve the stability, adhesion, wear and amount of drug delivery per unit area. The desirable composition is non-irritating to the skin. Further, the composition should be sufficiently adhesive so as to firmly adhere to the skin, even when subjected to adverse conditions such as humidity, perspiration, movement, showers and/or bathing, but not so adhesive as to cause irritation to the skin or substantial discomfort to the patient when removed from the skin. Further, all components used must be compatible with the drug.

The composition can also contain agents known to accelerate the release of the drug onto the body surface or through the skin. This class of agents includes those with diverse mechanisms of action including those which have the function of improving the solubility and diffusibility of the drug within the multipolymer and those which improve percutaneous absorption. For example, by changing the stratum corneum's (skin) ability to retain moisture, softening the skin, improving the skin's permeability, acting as penetration assistants or hair-follicle openers or changing the state of the skin including the boundary layer. Some of these agents have more than one mechanism of action and can, in addition, enhance the efficacy of the drug. Some examples of these release enhancers are glycols such as diethylene glycol, propylene glycol or polyethylene glycol which enhance drug solubility, oils such as olive oil, squalene or lanolin, fatty ethers such as cetyl ether and oleyl ether and fatty acid esters such as myristyl propriate which enhance drug diffusibility, urea and urea derivatives such as allantoin which affect the ability of keratin to retain moisture, polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability, salicylic acid which softens the keratin, amino acids which are penetration assistants, benzyl nicotinate which is a hair follicle opener, and higher molecular weight aliphatic surfactants such as lauryl sulfate salts which change the surface state of the skin and drugs administered, concomitantly which have good percutaneous absorption. Other agents include linoleic and ascorbic acids, panthenol, butylated hydroxytoluene, propyl oleate and propyl or isopropyl myristates.

Some drugs, such as the vasodilator nitroglycerin, function as a plasticizer because they are soluble to a certain degree in the polymer. For drug molecules which are not readily soluble in the polymer, a cosolvent for the drug and polymer can be added. Cosolvents, such as, lecithin, retinol derivatives, tocopherol, dipropylene glycol, triacetin, propylene glycol, saturated and unsaturated fatty acids, mineral oil, alcohols, butyl benzyl pthalate, etc. are useful cosolvents in the said invention depending on the solubility of the drug chosen. The adhesive polymer/drug compositions of the invention may then be combined with the crosslinking agent.

The composition of this invention may be combined with various thickeners, fillers and other additives known for use with transdermal compositions. Where the composition lends to absorb water, for example where lecithin is used as a co-solvent, hydrophilic fillers are especially useful. One type of hydrophilic filler which has been employed is a hydrated aluminum silicate clay, a substance not typical for transdermal formulation.

The adhesive layer is backed by a material useful for preventing the escape of active ingredients from the adhesive layer; however, the backing layer should not absorb the active ingredient. This backing layer is desirably selectively permeable, for example to oxygen, with a suitable water-vapor transmission rate so that the transdermal drug delivery system will "breathe", allowing the skin to maintain a more natural state. However the backing layer may be an occlusive material, such as, metal foil (example: aluminum), polyolefin (example: polyethylene or polypropylene), polyester (example: polyethylene terephthalate), and polyamid (example: nylon, as described in U.S. Pat. No. 4,291,015, the disclosure of which is incorporated by reference).

Preferred and optimum compositions are as follows:

TABLE

| Component | PERCENT BY WEIGHT | |
| --- | --- | --- |
|  | Optimum Amount | Preferred Range |
| Rubber | 5 | 2 to 20 |
| Acrylate | 47 | 25 to 70 |
| Ethylene-Vinyl Acetate | 5 | 3 to 20 |
| Polyisobutylene | 12 | 3 to 20 |
| Lecithin | 4.5 | 1 to 10 |
| Propylene Glycol | 8 | 0 to 10 |
| Butylene Glycol | 3 | 0 to 10 |
| Dipropylene Glycol | 1 | 0 to 10 |
| Oleic Acid | 7 | 2 to 10 |
| Clay | 3 | 0 to 6 |
| Mineral Oil | 2 | 0 to 4 |
| Drug | 2.5 | .5 to 6 |
|  | 100.0% |  |

EXAMPLES

In the following examples, "Airflex" refers to a trademark of Air Products and Chemicals Inc., Allentown, Pa. for a group of optionally carboxylated vinyl acetate/ethylene polymers in aqueous emulsion. "Airflex 416" is a carboxylated vinyl acetate/ethylene terpolymer and has the following properties:

| Solids | 52% min. |
| --- | --- |
| Viscosity (cps) | 1500-2500 |
| pH | 3.5 to 5 |
| Density | 8.8 lbs. per gal. |

The same type of polymer, "Airflex 426" has the properties:

| Viscosity (20 rpm) (cps) | 1,000-1,500 |
| --- | --- |
| pH | 4.5-5.0 |
| Tg (°C.) | −5 to 0 |
| Intrinsic Viscosity In Toluene | 0.3-0.4 |
| Swell Index | 17.5-22.5 |

"Airflex 400", "Airflex 405" and "Airflex 465 DEV" are trademarks of Air Products and Chemicals Inc., Allentown, Pa. for a group of vinyl acetate/ethylene copolymers supplied as aqueous emulsions.

Airflex 400 has the following properties:

| Viscosity | 1900–2800 cps @ 20 rpm (77° F.) |
|---|---|
| Tg | 0° C. |
| pH | 4.0 to 5.0 |
| density | 8.9 lb per gal. |

Airflex 405 has the following properties:

| Viscosity | 300–1000 cps @ 20 rpm (25° C.) |
|---|---|
| Tg | 7° C. |
| pH | 5.0 to 6.0 |
| density | 9.0 lb per gal. |

Airflex 465 DEV has the following properties:

| Viscosity | 800–1300 cps @ 20 rpm (77° F.) |
|---|---|
| Tg | −5° C. |
| pH | 4.5 to 5.5 |
| density | 9.0 lb per gal. |

ELVAX 40-W is a trademark of Dupont for an ethylene/vinyl acetate polymer which has the following properties:

| Vinyl Acetate (VAc) Content, % by weight | 40 |
|---|---|
| Inherent Viscosity @ 30° C. (0.25 g/100 ml. toluene) | 0.70 |
| Melt Index, g/10 min. (ASTM D 1238, modified) | 57 |
| Residual VAc Monomer, % by wt. | about 0.3 |
| Odor | Slight |
| Antioxidant, ppm BHT | 550 |
| Tensile Strength$^a$, MPa (psi) | 4.8–6.2 (750–900) |
| Elongation at Break$^a$, % | 1000–1300 |
| Elastic (Tensile) Modulus$^{a,b}$, MPa (psi) | 3.0 (450) |
| Density @ 23° C. (73° F.), kg/m$^3$ (ASTM D 1505) (G/cm$^3$) | 965 (0.965) |
| Hardness, Shore A-2 Durometer, 10 sec (ASTM D 2240) | 40 |
| Softening Point, Ring and Ball, °C. (ASTM E 28) (°F.) | 104 (220) |

$^a$ASTM D 1708; samples die cut from pressed films; gage dimensions 2.23 cm × 0.47 cm × 0.13 cm (0.876 in × 0.187 in × 0.050 in); crosshead speed 5.1 cm (2 in)/min.
$^b$Modulus calculated as in ASTM D 638.

Hartex 103 is a trademark of Firestone Synthetic Rubber and Latex Company for low-ammonia natural latex (rubber) containing 0.036% sodium dimethyldithiocarbamate and 0.036% zinc oxide as a preservative. The properties of this latex are as follows:

| Total Solids | 62.1 ± 0.3 |
|---|---|
| | 61.5 min. |
| Dry Rubber Content, % | 60.0 min. |
| TS minus DRC, % | 1.75 max. |
| Total Alkalinity, % NH on wet weight | .24 ± .02 |
| KOH Number | 0.55 ± 0.05 |
| Mechanical Stability, sec. | 1400 ± 300 |
| Volatile Fatty Acid, % | 0.05 max. |
| pH | 9.8 ± 0.20 |
| Sludge Content, % on weight | 0.03 max. |

PSA 578A is the trademark of Dow Chemical, Midland, Mich. for carboxylated styrene/butadiene containing a bactericide and a stabilizer. The formulation has a boiling point of 100° C., a vapor pressure of 17.5 millimeters of mercury at 20° C., a Tg. at −44° C. a vapor density of 0.624 at 80° F., is supplied in emulsion form with a milky white liquid appearance and has a specific gravity of 0.980–1.040.

ADCOTE 72A103 is a trademark of Morton Thiokol, Chicago, Ill. for a styrene butadiene styrene block copolymer rubber.

Nitroglycerin can be supplied as glyceryltrinitrate available in an ethanol solution from Imperial Chemical Industries.

"Exxon 108A" emulsion is the trademark of Exxon Chemical Company, Baton Rouge, La. for an aliphatic petroleum resin tackifying agent having a glass transition temperature of 40° C., a pH of 7.0 and an average particle size of 0.33 microns, and an anionic particle charge.

"Exxon 109A" emulsion is the trademark of Exxon Chemical Company, Baton Rouge, La. for a mixed aromatic/aliphatic petroleum resin tackifying agent in an aqueous emulsion having a glass transition temperature (Tg) at 37° C., a pH of 7.0, with an average particle size of 0.5 microns and an anionic particle charge.

"Noven 109A" is a trademark of Noven Pharmaceuticals, Inc., Miami, Fla., for the combination of 140 parts of the anhydrous resin Exxon 109A, 70 parts toluene and 7 parts Triton X-100. Triton X-100 is a trademark of Rohm and Haas Company for the water soluble, anhydrous, nonionic surfactant octylphenoxypolyethoxyethanol with an average of 10 moles of ethylene oxide, having a viscosity of 240 cps @ 25° C. (Brookfield), a pour point of 7° C. or 45° F., a specific gravity of 1.065 @ 25° C. and a density of 8.9 lb. per gallon.

"Exxon 346" is a trademark of Exxon Chemical Company for a mixed aromatic/aliphatic petroleum resin tackifying agent having a Tg of 25° C., a pH of 7.0, an average particle size of 0.35 microns and an anionic particle charge.

VISTANEX LM-MS-LC is trademark of Exxon Chemical Company, Houston, Tex. for a polyisobutylene having a Flory Molecular Weight of 37,000 minimum by AMS Test Method 77-005, a specific gravity of 0.91 and a Brookfield Viscosity, CPS @ 350° F., of 26,000 to 35,000 by ASTM Text Method 03236.

Hatcol 200 is a trademark of Hatco Chemical Company, Fords, N.J., for a high molecular weight synthetic ester plasticizer having a molecular weight of 546 and a viscosity @ 20° C. of 300 CPS.

"Korthix H-NF" is a trademark of Kaopolite, Inc., Union, N.J. for bentonite, a colloidal aluminum silicate (clay).

"Escorez Resin 1310LC and 2101 and 2393" are a trademark of Exxon Chemical Company, Baton Rouge, La. for aliphatic (1310LC) and aliphatic/aromatic (2101 & 2393) resins functioning as a tackifier.

Duro-Tak 36-6172 is a trademark of National Starch and Chemical Corporation, Bridgewater, N.J. for a solution of a resin modified styrene butadiene block copolymer with terpene resins and rosin ester resins having softening points of 100° C.

"Duro-Tak 80-1194 and 80-1196 and 80-1054" are a trademark of National Starch for a polyacrylate in organic solution.

"Duro-Tak 80-1194 and 80-1196" consists of methacrylic acid, 0–3%, butyl acrylate, 2 ethylhexyl acrylate and other monomers, such as, vinyl acetate.

"Flexbond 150" is a trademark of Air Products and Chemicals, Inc., Allentown, Pa. for a polyvinylacetate polymer which is a pressure sensitive emulsion which can function as a tackifying agent.

"Aerotex 3730" resin is a trademark of American Cyanamid, Wayne, N.Y. for a melamine formaldehyde crosslinking agent for various functional groups, including carboxyl groups having a density of 10.5 lbs. per gallon.

"Santicizer 160" is a trademark of Monsanto, St. Louis, Mo. for butyl benzyl phthalate.

All the polymeric ingredients used in the examples are supplied as aqueous emulsions or as solutions wherein the percent solids are as follows:

| Ingredient | Percent Solids |
|---|---|
| Airflex 400 | 55% |
| Airflex 405 | 55 |
| Airflex 416 | 52 |
| Airflex 426 | 60 |
| Airflex 465 | 66 |
| Hartex 103 | 61.5 |
| PSA 578A | 49 |
| Exxon 108A | 57 |
| Exxon 109A | 57 |
| Exxon 346 | 57 |
| Noven 109A | 35 |
| Flexbond 150 | 55 |
| Aerotex 3730 | 83 |
| Duro-Tak 36-6172 | 56 |
| Duro-Tak 80-1194 | 45 |
| Adcote 72A103 | 45 |

The general method of preparation of the adhesive is per the following steps:

1. Appropriate amounts of rubber, tackifying agent and multipolymer are combined, and thoroughly mixed together in a vessel;
2. The homogeneous mixture is then transferred to a vessel where the drug or drug and cosolvent are to be added;
3. The drug is then added to the homogeneous mixture and agitation is carried out until the mixture and drug form a smooth, homogeneous mix;
4. The homogeneous mix containing the drug is then transferred to an adhesive mixing vessel;
5. The mix containing the drug can then be combined with a crosslinking agent and any additional optional ingredients and thoroughly agitated;
6. The adhesive containing the drug is then transferred to a coating operation;
7. The adhesive composition containing the drug is now in a form to make up the adhesive layer to be coated onto a release liner. When the adhesive composition has been coated onto the release liner, the unit is then passed into an oven in order to drive off the solvents and/or water which may have been included in the mixing procedure; and after this operation is completed and the solvents are removed, the adhesive-component layer will be joined to the backing material and the unit can be wound into rolls for storage.

The order of steps, the amount of the ingredients, pH, and the amount and time of agitation or mixing may be important to avoiding clumping together of the components. These factors can be adjusted by those skilled in the art, while keeping in mind the object of providing a smooth, homogeneous mix. It is believed that a number of other methods, including changing some of the order of steps, can be carried out and will give desirable results. In addition to having various shapes, the dosage units produced may come in various sizes. A surface area in the range of 1 to 200 square centimeters is contemplated and the presently contemplated, preferred sizes are: 5, 10, 15, 20, 30, 40 and 60 square centimeters. The present invention allows incorporation of the amount of drug that is sufficient to deliver the required dose, no greater than the amount that would yield undesirable properties.

EXAMPLES

In the following examples, percent refers to percent by weight (dry).

Example 1

The mixture of 5 parts of a rubber (ADCOTE 72A103), 58.5 parts of a pressure sensitive acrylic solution (DURO-TAK 80-1194), 5 parts of ethylene vinyl acetate (ELVAX 40W), 9 parts of polyisobutylene, 7.5 parts of oleic acid, 5 parts of lecithin, 5 parts of propylene glycol and 3 parts of butylene glycol and 2 parts of estradiol are mixed slowly with stirring. The resulting mixture is coated onto a release liner.

The resulting composition has the following ingredients in the indicated amount.

| COMPONENT | PERCENT BY WEIGHT |
|---|---|
| 1. Rubber ADCOTE 72A103 | 5.0 |
| 2. Acrylic DURO-TAK 80-1194 | 58.5 |
| 3. Ethylene Vinyl Acetate ELVAX 40W | 5.0 |
| 4. Tackifier Polyisobutylene-VISTANEX LM-MS-LC | 9.0 |
| 5. Plasticizer Oleic Acid | 7.5 |
| 6. Dispersing Agent Lecithin | 5.0 |
| 7. Solvent Propylene Glycol | 5.0 |
| 8. Solvent Butylene Glycol | 3.0 |
| 9. Drug Estradiol | 2.0 |
| | 100.0 |

Example 2

In the following examples, the method of Example 1 is used with the appropriate starting material to yield compositions having the following ingredients:

| COMPONENT | PERCENT BY WEIGHT |
|---|---|
| 1. Ethylene Vinyl Acetate ELVAX 40W | 5.0 |
| 2. Rubber Duro-Tak 36-6172 | 5.0 |
| 3. Acrylic Duro-Tak 80-1194 | 37.0 |
| 4. Resin Escorez 2101 | 9.0 |
| 5. Solvent Propylene Glycol | 30.0 |
| 6. Plasticizer Oleic Acid | 10.0 |
| 7. Dispersing Agent Allantoin | 1.0 |
| 8. Plasticizer Hatcol 300 | 2.0 |
| 9. Drug Estradiol | 1.0 |
| | 100.0 |

Example 3

| COMPONENT | PERCENT BY WEIGHT |
|---|---|
| 1. Ethylene Vinyl Acetate ELVAX 40W | 10.0 |
| 2. Rubber Duro-Tak 36-6172 | 10.0 |
| 3. Acrylic Duro-Tak 80-1194 | 29.0 |
| 4. Resin Escorez 2101 | 5.0 |
| 5. Solvent Propylene Glycol | 30.0 |
| 6. Plasticizer Oleic Acid | 10.0 |
| 7. Dispersing Agent Allantoin | 1.0 |
| 8. Plasticizer Hatcol 200 | 4.0 |
| 9. Drug Estradiol | 1.0 |
| | 100.0 |

Example 4

| COMPONENT | PERCENT BY WEIGHT |
|---|---|
| 1. Ethylene Vinyl Acetate ELVAX | 10.0 |
| 2. Rubber Duro-Tak 36-6172 | 20.0 |
| 3. Solvent Propylene Glycol | 30.0 |
| 4. Plasticizer Oleic Acid | 10.0 |
| 5. Acrylic Duro-Tak 80-1194 | 29.0 |
| 6. Drug Estradiol | 1.0 |
| | 100.0 |

Example 5

| COMPONENT | PERCENT BY WEIGHT |
|---|---|
| 1. Ethylene Vinyl Acetate ELVAX 40W | 15.0 |
| 2. Rubber Duro-Tak 36-6172 | 15.0 |
| 3. Solvent Propylene Glycol | 30.0 |
| 4. Plasticizer Oleic Acid | 10.0 |
| 5. Acrylic Duro-Tak 80-1194 | 29.0 |
| 6. Drug Estradiol | 1.0 |
| | 100.0 |

Example 6

| COMPONENT | PERCENT BY WEIGHT |
|---|---|
| 1. Ethylene Vinyl Acetate ELVAX 40W | 10.0 |
| 2. Rubber Duro-Tak 36-6172 | 10.0 |
| 3. Solvent Propylene Glycol | 30.0 |
| 4. Plasticizer Oleic Acid | 10.0 |
| 5. Acrylic Duro-Tak 80-1194 | 29.0 |
| 6. Resin Escorez 2101 | 10.0 |
| 7. Drug Estradiol | 1.0 |
| | 100.0 |

Example 7

| COMPONENT | PERCENT BY WEIGHT |
|---|---|
| 1. Ethylene Vinyl Acetate ELVAX 40W | 15.0 |
| 2. Rubber Duro-Tak 36-6172 | 16.0 |
| 3. Solvent Propylene Glycol | 30.0 |
| 4. Plasticizer Oleic Acid | 10.0 |
| 5. Acrylic Duro-Tak 80-1194 | 27.3 |
| 6. Dispersing Agent Allantoin | .7 |
| 7. Drug Estradiol | 1.0 |
| | 100.0 |

Example 8

| COMPONENT | PERCENT BY WEIGHT |
|---|---|
| 1. Plasticizer Oleic Acid | 14.0 |
| 2. Solvent Propylene Glycol | 14.0 |
| 3. Acrylic Duro-Tak 80-1194 | 2.0 |
| 4. Acrylic Duro-Tak 80-1054 | 38.0 |
| 5. Plasticizer Santicizer 160 | 30.0 |
| 6. Drug Estradiol | 2.0 |
| | 100.0 |

Example 9

| COMPONENT | PERCENT BY WEIGHT |
|---|---|
| 1. Plasticizer Oleic Acid | 14.0 |
| 2. Solvent Propylene Glycol | 14.0 |
| 3. Acrylic Duro-Tak 80-1194 | 32.0 |
| 4. Acrylic Duro-Tak 80-1054 | 2.0 |
| 5. Plasticizer Santicizer 160 | 30.0 |
| 6. Drug Estradiol | 2.0 |
| | 100.0 |

Example 10

| COMPONENT | PERCENT BY WEIGHT |
|---|---|
| 1. Ethylene Vinyl Acetate ELVAX 40W | 18.0 |
| 2. Rubber Duro-Tak 36-6172 | 10.0 |
| 3. Acrylic Duro-Tak 80-1194 | 23.0 |
| 4. Solvent Propylene Glycol | 30.0 |
| 5. Plasticizer Oleic Acid | 10.0 |
| 6. Drug | 2.0 |

-continued

| COMPONENT | PERCENT BY WEIGHT |
|---|---|
| Estradiol | |
| 7. Resin | 5.0 |
| Escorez 2393 | |
| 8. Dispersing Agent | 2.0 |
| Allantoin | 100.0 |

Example 11

| COMPONENT | PERCENT BY WEIGHT |
|---|---|
| 1. Ethylene Vinyl Acetate | 18.0 |
| ELVAX 40W | |
| 2. Rubber | 10.0 |
| Duro-Tak 36-6172 | |
| 3. Acrylic | 23.0 |
| Duro-Tak 80-1194 | |
| 4. Resin | 5.0 |
| Escorez 2101 | |
| 5. Resin | 2.0 |
| Escorez 1310 LC | |
| 6. Dispersing Agent | 24.0 |
| Lecithin | |
| 7. Solvent | 16.0 |
| Medium Chain | |
| Triglyceride | |
| 8. Drug | 2.0 |
| Estradiol | 100.0 |

Example 12

| COMPONENT | PERCENT BY WEIGHT |
|---|---|
| 1. Ethylene Vinyl Acetate | 4.5 |
| ELVAX 40W | |
| 2. Carboxylated Vinyl | 22.5 |
| Acetate-Ethylene | |
| Airflex 416 | |
| 3. Rubber | 5.0 |
| Duro-Tak 36-6172 | |
| 4. Acrylic | 19.0 |
| Duro-Tak 80-1194 | |
| 5. Plasticizer | 10.0 |
| Oleic Acid | |
| 6. Solvent | 30.0 |
| Propylene Glycol | |
| 7. Dispersing Agent | 2.0 |
| Allantoin | |
| 8. Drug | 1.0 |
| Estradiol | |
| 9. Resin | 6.0 |
| Escorez 1310 LC | 100.0 |

Example 13

| COMPONENT | PERCENT BY WEIGHT |
|---|---|
| 1. Ethylene Vinyl Acetate | 7.5 |
| ELVAX 40W | |
| 2. Rubber | 2.5 |
| Duro-Tak 36-6172 | |
| 3. Acrylic | 37.0 |
| Duro-Tak 80-1194 | |
| 4. Resin | 7.0 |
| Escorez 2101 | |
| 5. Solvent | 30.0 |
| Propylene Glycol | |
| 6. Plasticizer | 10.0 |
| Oleic Acid | |
| 7. Dispersing Agent | 1.0 |
| Allantoin | |
| 8. Drug | 3.0 |

-continued

| COMPONENT | PERCENT BY WEIGHT |
|---|---|
| Estradiol | 100.0 |

Example 14

| COMPONENT | PERCENT BY WEIGHT |
|---|---|
| 1. Ethylene Vinyl Acetate | 7.5 |
| ELVAX 40W | |
| 2. Rubber | 2.5 |
| Duro-Tak 36-6172 | |
| 3. Acrylic | 40.0 |
| Duro-Tak 80-1194 | |
| 4. Resin | 7.0 |
| Escorez 2101 | |
| 5. Plasticizer | 10.0 |
| Oleic Acid | |
| 6. Dispersing Agent | 1.0 |
| Allantoin | |
| 7. Drug | 2.0 |
| Estradiol | |
| 8. Solvent | 30.0 |
| Dipropylene Glycol | 100.0 |

Example 15

| COMPONENT | PERCENT BY WEIGHT |
|---|---|
| 1. Ethylene Vinyl Acetate | 7.5 |
| ELVAX 40W | |
| 2. Rubber | 2.5 |
| Duro-Tak 36-6172 | |
| 3. Acrylic | 40.0 |
| Duro-Tak 80-1194 | |
| 4. Resin | 7.0 |
| Escorez 2101 | |
| 5. Plasticizer | 10.0 |
| Oleic Acid | |
| 6. Dispersing Agent | 1.0 |
| Allantoin | |
| 7. Drug | 2.0 |
| Estradiol | |
| 8. Solvent | 30.0 |
| Polyethylene Glycol | 100.0 |

Example 16

| COMPONENT | PERCENT BY WEIGHT |
|---|---|
| 1. Ethylene Vinyl Acetate | 7.5 |
| ELVAX 40W | |
| 2. Rubber | 2.5 |
| Duro-Tak 36-6172 | |
| 3. Acrylic | 39.0 |
| Duro-Tak 80-1194 | |
| 4. Resin | 8.0 |
| Escorez 2101 | |
| 5. Solvent | 30.0 |
| Propylene Glycol | |
| 6. Plasticizer | 10.0 |
| Oleic Acid | |
| 7. Dispersing Agent | 1.0 |
| Allantoin | |
| 8. Drug | 1.0 |
| Estradiol | |
| 9. Hydrophil | 1.0 |
| Carboxymethyl | 100.0 |
| Cellulose | |

Example 17

| COMPONENT | PERCENT BY WEIGHT |
|---|---|
| 1. Rubber ADCOTE 72A103 | 5.0 |
| 2. Acrylic Duro-Tak 80-1194 | 51.0 |
| 3. Ethylene Vinyl Acetate ELVAX 40W | 5.0 |
| 4. Tackifier Polyisobutylene - Vistanex LM-MS-LC | 12.0 |
| 5. Plasticizer Oleic Acid | 7.0 |
| 6. Dispersing Agent Lecithin | 7.5 |
| 7. Solvent Butylene Glycol | 7.0 |
| 9. Clay Korthix H-NF | 3.0 |
| 10. Drug Estradiol | 2.5 |
| | 100.0 |

Example 18

| COMPONENT | PERCENT BY WEIGHT |
|---|---|
| 1. Rubber ADCOTE 72A103 | 5.0 |
| 2. Acrylic Duro-Tak 80-1194 | 53.0 |
| 3. Ethylene Vinyl Acetate ELVAX 40W | 5.0 |
| 4. Tackifier Polyisobutylene - Vistanex LM-MS-LC | 12.0 |
| 5. Plasticizer Oleic Acid | 7.0 |
| 6. Dispersing Agent Lecithin | 4.5 |
| 7. Solvent Propylene Glycol | 3.0 |
| 8. Solvent Butylene Glycol | 3.0 |
| 9. Solvent Dipropylene Glycol | 2.0 |
| 10. Clay Korthix H-NF | 3.0 |
| 11. Drug Estradiol | 2.5 |
| | 100.0 |

Example 19

| COMPONENT | PERCENT BY WEIGHT |
|---|---|
| 1. Rubber ADCOTE 72A103 | 5.0 |
| 2. Acrylic Duro-Tak 80-1194 | 52.0 |
| 3. Ethylene Vinyl Acetate ELVAX 40W | 5.0 |
| 4. Tackifier Polyisobutylene - Vistanex LM-MS-LC | 12.0 |
| 5. Plasticizer Oleic Acid | 7.0 |
| 6. Dispersing Agent Lecithin | 4.5 |
| 7. Solvent Propylene Glycol | 3.0 |
| 8. Solvent Dipropylene Glycol | 6.0 |
| 9. Clay Korthix H-NF | 3.0 |
| 10. Drug Estradiol | 2.5 |
| | 100.0 |

Example 20

| COMPONENT | PERCENT BY WEIGHT |
|---|---|
| 1. Rubber ADCOTE 72A103 | 5.0 |
| 2. Acrylic Duro-Tak 80-1194 | 52.0 |
| 3. Ethylene Vinyl Acetate ELVAX 40W | 5.0 |
| 4. Tackifier Polyisobutylene-Vistanex LM-MS-LC | 12.0 |
| 5. Plasticizer Oleic Acid | 7.0 |
| 6. Dispersing Agent Lecithin | 4.5 |
| 7. Solvent Propylene Glycol | 3.0 |
| 8. Solvent Butylene Glycol | 5.0 |
| 9. Solvent Dipropylene Glycol | 1.0 |
| 10. Clay Korthix H-NF | 3.0 |
| 11. Drug Estradiol | 2.5 |
| | 100.0 |

Example 21

| COMPONENT | PERCENT BY WEIGHT |
|---|---|
| 1. Rubber ADCOTE 72A103 | 5.0 |
| 2. Acrylic Duro-Tak 80-1194 | 47.0 |
| 3. Ethylene Vinyl Acetate ELVAX 40W | 5.0 |
| 4. Tackifier Polyisobutylene-Vistanex LM-MS-LC | 12.0 |
| 5. Plasticizer Oleic Acid | 7.0 |
| 6. Dispersing Agent Lecithin | 4.5 |
| 7. Solvent Propylene Glycol | 10.0 |
| 8. Solvent Butylene Glycol | 3.0 |
| 9. Clay Korthix H-NF | 3.0 |
| 10. Solvent Mineral Oil | 1.0 |
| 11. Drug Estradiol | 2.5 |
| | 100.0 |

Example 22

| COMPONENT | PERCENT BY WEIGHT |
|---|---|
| 1. Rubber ADCOTE 72A103 | 5.0 |
| 2. Acrylic Duro-Tak 80-1194 | 49.0 |
| 3. Ethylene Vinyl Acetate ELVAX 40W | 5.0 |
| 4. Tackifier Polyisobutylene-Vistanex LM-MS-LC | 12.0 |
| 5. Plasticizer Oleic Acid | 7.0 |

-continued

| COMPONENT | PERCENT BY WEIGHT |
|---|---|
| 6. Dispersing Agent<br>Lecithin | 4.5 |
| 7. Solvent<br>Propylene Glycol | 8.0 |
| 8. Solvent<br>Butylene Glycol | 3.0 |
| 9. Clay<br>Korthix H-NF | 3.0 |
| 10. Solvent<br>Mineral Oil | 1.0 |
| 11. Drug<br>Estradiol | 2.5 |
| | 100.0 |

Example 23

| COMPONENT | PERCENT BY WEIGHT |
|---|---|
| 1. Rubber<br>ADCOTE 72A103 | 5.0 |
| 2. Acrylic<br>Duro-Tak 80-1194 | 51.0 |
| 3. Ethylene Vinyl Acetate<br>ELVAX 40W | 5.0 |
| 4. Tackifier<br>Polyisobutylene-Vistanex LM-MS-LC | 12.0 |
| 5. Dispersing Agent<br>Lecithin | 4.5 |
| 6. Solvent<br>Propylene Glycol | 6.0 |
| 7. Solvent<br>Butylene Glycol | 3.0 |
| 8. Plasticizer<br>Oleic Acid | 6.0 |
| 9. Clay<br>Korthix H-NF | 3.0 |
| 10. Solvent<br>Mineral Oil | 2.0 |
| 11. Drug<br>Estradiol | 2.5 |
| | 100.0 |

Example 24

| COMPONENT | PERCENT BY WEIGHT |
|---|---|
| 1. Rubber<br>ADCOTE 72A103 | 5.0 |
| 2. Acrylic<br>Duro-Tak 80-1194 | 51.0 |
| 3. Ethylene Vinyl Acetate<br>ELVAX 40W | 5.0 |
| 4. Tackifier<br>Polyisobutylene-Vistanex LM-MS-LC | 12.0 |
| 5. Dispersing Agent<br>Lecithin | 4.5 |
| 6. Solvent<br>Propylene Glycol | 7.0 |
| 7. Solvent<br>Butylene Glycol | 3.0 |
| 8. Plasticizer<br>Oleic Acid | 6.0 |
| 9. Clay<br>Korthix H-NF | 3.0 |
| 10. Solvent<br>Mineral Oil | 1.0 |
| 11. Drug<br>Estradiol | 2.5 |
| | 100.0 |

Example 25

| COMPONENT | PERCENT BY WEIGHT |
|---|---|
| 1. Rubber<br>ADCOTE 72A103 | 5.0 |
| 2. Acrylic<br>Duro-Tak 80-1194 | 50.5 |
| 3. Ethylene Vinyl Acetate<br>ELVAX 40W | 5.0 |
| 4. Tackifier<br>Polyisobutylene-Vistanex LM-MS-LC | 12.0 |
| 5. Plasticizer<br>Oleic Acid | 7.5 |
| 6. Dispersing Agent<br>Lecithin | 4.5 |
| 7. Solvent<br>Propylene Glycol | 7.0 |
| 8. Solvent<br>Butylene Glycol | 3.0 |
| 9. Clay<br>Korthix H-NF | 3.0 |
| 10. Drug<br>Estradiol | 2.5 |
| | 100.0 |

Example 26

| COMPONENT | PERCENT BY WEIGHT |
|---|---|
| 1. Rubber<br>ADCOTE 72A103 | 5.0 |
| 2. Acrylic<br>Duro-Tak 80-1194 | 53.0 |
| 3. Ethylene Vinyl Acetate<br>ELVAX 40W | 5.0 |
| 4. Tackifier<br>Polyisobutylene-Vistanex LM-MS-LC | 12.0 |
| 5. Plasticizer<br>Oleic Acid | 5.0 |
| 6. Dispersing Agent<br>Lecithin | 4.5 |
| 7. Solvent<br>Propylene Glycol | 7.0 |
| 8. Solvent<br>Butylene Glycol | 3.0 |
| 9. Clay<br>Korthix H-NF | 3.0 |
| 10. Drug<br>Estradiol | 2.5 |
| | 100.0 |

Example 27

| COMPONENT | PERCENT BY WEIGHT |
|---|---|
| 1. Rubber<br>ADCOTE 72A103 | 5.0 |
| 2. Acrylic<br>Duro-Tak 80-1196 | 47.0 |
| 3. Ethylene Vinyl Acetate<br>ELVAX 40W | 5.0 |
| 4. Tackifier<br>Polyisobutylene-Vistanex LM-MS-LC | 12.0 |
| 5. Plasticizer<br>Oleic Acid | 7.0 |
| 6. Dispersing Agent<br>Lecithin | 4.5 |
| 7. Solvent<br>Propylene Glycol | 4.0 |
| 8. Solvent<br>Dipropylene Glycol | 5.0 |
| 9. Solvent<br>Butylene Glycol | 3.0 |
| 10. Clay<br>Korthix H-NF | 3.0 |

-continued

| COMPONENT | PERCENT BY WEIGHT |
|---|---|
| 11. Solvent Mineral Oil | 2.0 |
| 12. Drug Estradiol | 2.5 |
| | 100.0 |

Example 28

| COMPONENT | PERCENT BY WEIGHT |
|---|---|
| 1. Rubber ADCOTE 72A103 | 5.0 |
| 2. Acrylic Duro-Tak 80-1196 | 51.0 |
| 3. Ethylene Vinyl Acetate ELVAX 40W | 5.0 |
| 4. Tackifier Polyisobutylene-Vistanex LM-MS-LC | 12.0 |
| 5. Plasticizer Oleic Acid | 7.0 |
| 6. Dispersing Agent Lecithin | 4.5 |
| 7. Solvent Propylene Glycol | 5.0 |
| 8. Solvent Dipropylene Glycol | 6.0 |
| 9. Clay Korthix H-NF | 3.0 |
| 10. Solvent Mineral Oil | 1.0 |
| 11. Drug Estradiol | 2.5 |
| | 100.0 |

Example 29

| COMPONENT | PERCENT BY WEIGHT |
|---|---|
| 1. Rubber ADCOTE 72A103 | 5.0 |
| 2. Acrylic Duro-Tak 80-1196 | 48.0 |
| 3. Ethylene Vinyl Acetate ELVAX 40W | 5.0 |
| 4. Tackifier Polyisobutylene-Vistanex LM-MS-LC | 12.0 |
| 5. Plasticizer Oleic Acid | 7.0 |
| 6. Dispersing Agent Lecithin | 4.5 |
| 7. Solvent Propylene Glycol | 5.0 |
| 8. Solvent Dipropylene Glycol | 6.0 |
| 9. Clay Korthix H-NF | 3.0 |
| 10. Solvent Mineral Oil | 2.0 |
| 11. Drug Estradiol | 2.5 |
| | 100.0 |

Example 30

| COMPONENT | PERCENT BY WEIGHT |
|---|---|
| 1. Ethylene Vinyl Acetate ELVAX 40W | 18.0 |
| 2. Rubber Duro-Tak 36-6172 | 10.0 |
| 3. Acrylic Duro-Tak 80-1194 | 23.0 |

-continued

| COMPONENT | PERCENT BY WEIGHT |
|---|---|
| 4. Resin Escorez 2101 | 5.0 |
| 6. Solvent Propylene Glycol | 32.0 |
| 7. Plasticizer Oleic Acid | 10.0 |
| 8. Drug Estradiol | 2.0 |
| | 100.0 |

Example 31

| COMPONENT | PERCENT BY WEIGHT |
|---|---|
| 1. Ethylene Vinyl Acetate ELVAX 40W | 18.0 |
| 2. Rubber Duro-Tak 36-6172 | 10.0 |
| 3. Acrylic Duro-Tak 80-1194 | 24.0 |
| 4. Resin Escorez 2101 | 5.0 |
| 5. Plasticizer Oleic Acid | 10.0 |
| 6. Drug Estradiol | 1.0 |
| 7. Dispersing Agent Allantoin | 2.0 |
| 9. Solvent Butylene Glycol | 30.0 |
| | 100.0 |

Example 32

The carboxylated vinyl acetate ethylene copolymer (Airflex 416) is adjusted to a pH of 5.0 with aqueous ammonia. This mixture is added slowly and with stirring to the rubber. Then, slowly add the tackifying agent and stir. Next the drug is added slowly and with stirring. And finally, any crosslinking agent is added and the mixture stirred. The resulting mixture is coated on to a release liner as set forth in step 7 above.

The resulting composition has the following ingredients in the indicated amounts.

| COMPONENT | PERCENT BY WEIGHT |
|---|---|
| Carboxylated Vinyl Acetate Ethylene Copolymer (Airflex 416) | 31.4 |
| Rubber (PSA 578A) | 8.8 |
| Tackifying Agent (Noven 109A) | 12.6 |
| Drug (nitroglycerin) | 42.2 |
| Water | 5.0 |
| | 100.0 |

In the following examples the method of Example 32 is used with the appropriate amounts of starting materials to yield compositions having the following ingredients.

Example 33

| COMPONENT | PERCENT BY WEIGHT |
|---|---|
| Carboxylated Vinyl Acetate-Ethylene Copolymer (Airflex 416) | 28.3 |
| Rubber (Hartex 103) | 10.0 |
| Tackifying Agent (Exxon 346) | 18.5 |
| Drug (nitroglycerin) | 38.0 |
| Crosslinking Agent (Aerotex 3730) | 0.2 |
| Water | 5.0 |

-continued

| COMPONENT | PERCENT BY WEIGHT |
|---|---|
| | 100.0 |

Example 34

| COMPONENT | PERCENT BY WEIGHT |
|---|---|
| Carboxylated Vinyl Acetate-Ethylene Copolymer (Airflex 416) | 28.8 |
| Rubber (PSA 578A) | 8.2 |
| Tackifying Agent (Exxon 346) | 19.0 |
| Drug (nitroglycerin) | 38.9 |
| Crosslinking Agent (Aerotex 3730) | 0.1 |
| Water | 5.0 |
| | 100.0 |

Example 35

| COMPONENT | PERCENT BY WEIGHT |
|---|---|
| Carboxylated Vinyl Acetate-Ethylene Copolymer (Airflex 416) | 29.6 |
| Rubber (PSA 578A) | 8.3 |
| Tackifying Agent (Flexbond 150) | 18.7 |
| Drug (nitroglycerin) | 38.0 |
| Crosslinking Agent (Aerotex 3730) | 0.4 |
| Water | 5.0 |
| | 100.0 |

Example 36

| COMPONENT | PERCENT BY WEIGHT |
|---|---|
| Carboxylated Vinyl Acetate-Ethylene Copolymer (Airflex 416) | 28.9 |
| Rubber (Hartex 103) | 10.2 |
| Tackifying Agent (Flexbond 150) | 18.3 |
| Drug (nitroglycerin) | 37.1 |
| Crosslinking Agent (Aerotex 3730) | 0.5 |
| Water | 5.0 |
| | 100.0 |

Example 37

| COMPONENT | PERCENT BY WEIGHT |
|---|---|
| Carboxylated Vinyl Acetate-Ethylene Copolymer (Airflex 426) | 28.3 |
| Rubber (Hartex 103) | 10.0 |
| Tackifying Agent (Exxon 109A) | 18.6 |
| Drug (Nitroglycerin) | 38.0 |
| Crosslinking Agent (Aerotex 3730) | 0.1 |
| Water | 5.0 |
| | 100.0 |

Example 38

| COMPONENT | PERCENT BY WEIGHT |
|---|---|
| Carboxylated Vinyl Acetate-Ethylene Copolymer (Airflex 416) | 28.6 |
| Rubber (Hartex 103) | 5.1 |
| Rubber (PSA 578A) | 4.0 |
| Tackifying Agent (Exxon 109A) | 18.8 |
| Drug (Nitroglycerin) | 38.4 |
| Crosslinking Agent (Aerotex 3730) | 0.1 |
| Water | 5.0 |

-continued

| COMPONENT | PERCENT BY WEIGHT |
|---|---|
| | 100.0 |

Example 39

| COMPONENT | PERCENT BY WEIGHT |
|---|---|
| Carboxylated Vinyl Acetate-Ethylene Copolymer (Airflex 416) | 28.8 |
| Rubber (PSA 578A) | 8.2 |
| Tackifying Agent (Exxon 108A) | 19.0 |
| Drug (Nitroglycerin) | 38.9 |
| Crosslinking Agent (Aerotex 3730) | 0.1 |
| Water | 5.0 |
| | 100.0 |

Example 40

| COMPONENT | PERCENT BY WEIGHT |
|---|---|
| Carboxylated Vinyl Acetate-Ethylene Copolymer (Airflex 416) | 29.0 |
| Rubber (Hartex 103) | 10.3 |
| Tackifying Agent (Flexbond 150) | 18.4 |
| Drug (Nitroglycerin) | 37.3 |
| Water | 5.0 |
| | 100.0 |

Example 41

| COMPONENT | PERCENT BY WEIGHT |
|---|---|
| Vinyl Acetate-Ethylene Copolymer (Airflex 465) | 39.5 |
| Rubber (Hartex 103) | 11.0 |
| Tackifying Agent (Exxon 109A) | 20.5 |
| Drug (Nitroglycerin) | 24.0 |
| Water | 5.0 |
| | 100.0 |

Example 42

| COMPONENT | PERCENT BY WEIGHT |
|---|---|
| Vinyl Acetate Ethylene Copolymer (Airflex 400) | 53.5 |
| Rubber (PSA 578A) | 14.3 |
| Drug (Nitroglycerin) | 27.2 |
| Water | 5.0 |
| | 100.0 |

Example 43

| COMPONENT | PERCENT BY WEIGHT |
|---|---|
| Vinyl Acetate Ethylene Copolymer (Airflex 405) | 35.0 |
| Rubber (Hartex 103) | 11.7 |
| Tackifying Agent (Exxon 109A) | 21.8 |
| Drug (Nitroglycerin) | 26.5 |
| Water | 5.0 |
| | 100.0 |

Example 44

| COMPONENT | PERCENT BY WEIGHT |
| --- | --- |
| Carboxylated Vinyl Acetate-Ethylene Copolymer (Airflex 416) | 34.0 |
| Rubber (Hartex 103) | 12.1 |
| Tackifying Agent (Exxon 109A) | 22.4 |
| Drug (Nitroglycerin) | 26.5 |
| Water | 5.0 |
|  | 100.0 |

Example 45

| COMPONENT | PERCENT BY WEIGHT |
| --- | --- |
| Carboxylated Vinyl Acetate-Ethylene terpolymer (Airflex 416) | 28.2 |
| Rubber (Hartex 103) | 10.0 |
| Tackifying agent (Exxon 109A) | 18.6 |
| Plasticizer (Santicizer 160) | 36.1 |
| drug (estradiol) | 1.9 |
| crosslinking agent (Aerotex 3730) | 0.2 |
| water | 5.0 |
|  | 100.0 |

Example 46

A formulation identical to that of Example 45 is prepared except that the amount of plasticizer is reduced to 30.4% and propylene glycol is added as solvent for the estradiol in the amount of 5.7 parts.

The dosage unit of the present invention can be produced in a number of ways. It is particularly important to form the adhesive layer in a series of steps, with proper agitation and pH adjustment when necessary, so as to avoid coagulation and clumping together of any of the components. After the adhesive layer is formed, the composition making up this layer can be placed in contact with the backing layer in any manner known to those skilled in the art in order to produce the transdermal dosage system. The transdermal dosage system can be produced as follows:

Generally speaking, known methods of producing adhesive tapes can be used for the composition of this invention. These known methods including calender coating method, hot melt coating method, solution coating method, emulsion coating method and radiation cured coating method. When dealing with explosive drugs such as nitroglycerin, the solution or emulsion coating method is preferred to minimize the risk of explosion or degradation.

In the calender coating method, the multipolymer, rubber, tackifier and other ingredients are kneaded homogeneously using open rolls, kneaders, internal mixers, etc. The materials of high viscosity have to be kneaded at elevated temperatures, usually 90 to 120° C. under high shear rate ($1 \times 10^3$ to $5 \times 10^3$ sec.$^{-1}$). In the hot melt coating method the substances with high thermal plasticity are added to the adhesives and the adhesives are coated at high velocity. In the emulsion coating method, the emulsion of the ingredients is added to the appropriate coating head and the excess solvent removed. The solution coating method is essentially the same as the emulsion coating method, except that the mixture is in solution rather than in an emulsion.

The backing member for the adhesive includes plastic films of polyethylene, vinyl acetate resins, ethylene/vinyl alcohol, ethylene/vinyl acetate copolymers, polyvinyl chloride, polyurethane, and the like, metal foils, for example aluminum foil, and the like, non-woven fabric, cloth and laminate films composed of cloth or paper and a basic film. The backing material preferably has a thickness of from 2 to 1,000 micrometers so as to have good handling properties and "feel". A total thickness of the film-like adhesive material on the backing member preferably ranges from 12 to 250 micrometers. Composite products having a total thickness less than 14 micrometers may have poor handling properties.

What is claimed is:

1. An adhesive dermal composition comprising a drug, a multipolymer containing vinyl acetate/ethylene polymer and an acrylic polymer, a natural or synthetic rubber, and a tackifying agent in which the ratio by weight of the multipolymer to the rubber is about 1:10 to about 30:1 and the ratio by weight of the vinyl acetate/ethylene polymer to the acrylic polymer is about 20:1 to about 1:20.

2. The dermal composition of claim 1, in which the ratio by weight of the multipolymer to a rubber is about 1:20 to about 20:1.

3. The dermal composition of claim 1, in which the multipolymer is an acrylic polymer and a vinyl acetate/ethylene copolymer and the rubber is polyisobutylene.

4. The dermal composition of claim 1 in which the drug is a solid or liquid at room temperature, is percutaneously absorbable, and is dissolved or dispersed in the composition.

5. The dermal composition of claim 4 in which the weight of the drug is about 0.1 to 50% by weight based on the weight of the dermal composition.

6. A dermal composition comprising a steroid, a multipolymer of an acrylic polymer and a vinyl acetate/ethylene copolymer, a natural or synthetic rubber, and a tackifying agent in which the multipolymer and rubber are in a ratio, respectively, of from about 1:1 to about 20:1.

7. The dermal composition according to claim 6 in which the acrylic polymer is selected from the group consisting of polymethacrylic acid and polyacrylic acid.

8. The dermal composition according to claim 6 in which the steroid is 17-Beta-Estradiol.

9. The dermal composition according to claim 6, in which the copolymer is a terpolymer of an ethylene/vinyl acetate copolymer and acrylic acid.

10. The dermal composition according to claim 9 in which the percent by weight of ethylene, vinyl acetate and acrylic acid units in the terpolymer are, respectively, roughly 15 to 90; 4 to 8 and 0 to 5.

11. The dermal composition according to claim 9 in which the amounts of ethylene, vinyl acetate and acrylic acid are respectively roughly 60%, 40% and 0%.

12. The dermal composition according to claim 6 in which the copolymer and natural or synthetic rubber are in a ratio, respectively, of about 1:3.

13. The dermal composition which comprises, as percent by weight, about 2% to about 10% ethylene/vinyl acetate copolymer, about 2% to about 20% natural or synthetic rubber, about 20% to about 60% of a polyacrylate about 5% to about 30% of a tackifying agent, and about 1% to about 50% of drug.

14. The composition according to claim 13 in which the drug is nitroglycerin or estradiol.

* * * * *

UNITED STATES PATENT AND TRADEMARK OFFICE
CERTIFICATE OF CORRECTION

PATENT NO.    : 4,994,267
DATED         : February 19, 1991
INVENTOR(S)   : Steven Sablotsky It is certified that error appears in the above-identified patent and that said Letters Patent is hereby corrected as shown below:

Column 26,
Line 51, "4 to 8" should read -- 4 to 80 --.

Signed and Sealed this

Twenty-eighth Day of December, 2004

JON W. DUDAS
*Director of the United States Patent and Trademark Office*